(12) United States Patent
Ford

(10) Patent No.: US 9,874,399 B2
(45) Date of Patent: Jan. 23, 2018

(54) CYLINDRICAL COMBUSTION TUBE AND MOUNTING ASSEMBLY

(71) Applicant: Leco Corporation, St. Joseph, MI (US)

(72) Inventor: Gordon C. Ford, St. Joseph, MI (US)

(73) Assignee: Leco Corporation, St. Joseph, MI (US)

( * ) Notice: Subject to any disclaimer, the term of this patent is extended or adjusted under 35 U.S.C. 154(b) by 650 days.

(21) Appl. No.: 14/508,315

(22) Filed: Oct. 7, 2014

(65) Prior Publication Data

US 2015/0023383 A1    Jan. 22, 2015

Related U.S. Application Data

(63) Continuation of application No. 12/889,628, filed on Sep. 24, 2010, now Pat. No. 8,884,193.

(Continued)

(51) Int. Cl.
| F27B 14/00 | (2006.01) |
| F05B 3/62 | (2006.01) |
| F27D 7/06 | (2006.01) |
| F27B 14/08 | (2006.01) |
| F27B 14/14 | (2006.01) |

(Continued)

(52) U.S. Cl.
CPC ............. *F27D 7/06* (2013.01); *F27B 14/061* (2013.01); *F27B 14/08* (2013.01); *F27B 14/14* (2013.01); *F27B 17/02* (2013.01); *F27D 11/06* (2013.01); *H05B 6/26* (2013.01); *F27B 2014/066* (2013.01); *F27B 2014/0825* (2013.01); *F27D 99/0073* (2013.01); *F27D 2007/063* (2013.01); *F27D 2201/00* (2013.01)

(58) Field of Classification Search
CPC .......... F27B 17/02; F27B 14/08; F27B 14/14; F27B 14/061; F27B 2014/066; F27B 2014/0825; F27D 7/06; F27D 11/06; F27D 99/0073; F27D 2007/063; F27D 2201/00; H05B 6/26

USPC ..... 373/7, 78, 129, 130, 138–142, 151, 152, 373/155, 157, 158; 422/78, 80.549; 219/426, 427, 430

See application file for complete search history.

(56) References Cited

U.S. PATENT DOCUMENTS 2,332,943 A    10/1943 Sobers
2,686,211 A    8/1954 Cargill
(Continued)

FOREIGN PATENT DOCUMENTS

JP    2000-266741 A    9/2000

OTHER PUBLICATIONS

Exploded view of prior art furance and combustion tube assembly and instructions for replacement of the combustion tube. (2 pages).

*Primary Examiner* — Hung D Nguyen
(74) *Attorney, Agent, or Firm* — Price Heneveld LLP

(57) ABSTRACT

A combustion tube mounting system releasably mounts a combustion tube to an aperture in the floor of a furnace housing. The combustion tube has a base assembly with a cam and can be manually or automatically unlocked by cam pins in the floor for selectively engaging the cam for lowering the combustion tube from the floor of the furnace. When a new combustion tube is placed on the lower seal assembly and raised, it automatically aligns and engages the upper furnace seal and engages cams on the floor of the furnace housing which lock the combustion tube in place as it is introduced into the furnace.

17 Claims, 13 Drawing Sheets

Related U.S. Application Data

(60) Provisional application No. 61/245,732, filed on Sep. 25, 2009.

(51) Int. Cl.
| | | |
|---|---|---|
| *F27B 17/02* | (2006.01) | |
| *F27D 11/06* | (2006.01) | |
| *F27B 14/06* | (2006.01) | |
| *H05B 6/26* | (2006.01) | |
| *F27D 99/00* | (2010.01) | |

(56) References Cited

U.S. PATENT DOCUMENTS

| | | |
|---|---|---|
| 2,809,100 A | 10/1957 | Krasl |
| 3,058,814 A | 10/1962 | Bennet |
| 3,812,705 A | 5/1974 | Boillot |
| 3,923,464 A | 12/1975 | Sitek et al. |
| 4,234,541 A | 11/1980 | Bredeweg et al. |
| 4,417,346 A * | 11/1983 | Giler ............... F27B 14/06 373/130 |
| 4,793,640 A | 12/1988 | Steward, Sr. |
| 5,720,091 A | 2/1998 | Garrett et al. |
| 6,101,212 A | 8/2000 | Hugo et al. |
| 6,803,237 B2 * | 10/2004 | Manganini ......... B01D 61/18 422/78 |
| 2011/0075696 A1 | 3/2011 | Ford |

* cited by examiner

CYLINDRICAL COMBUSTION TUBE AND MOUNTING ASSEMBLY

CROSS-REFERENCE TO RELATED APPLICATIONS

This application is a continuation of U.S. patent application Ser. No. 12/889,628, filed Sep. 24, 2010, entitled EASILY REMOVABLE COMBUSTION TUBE, which claimed priority under 35 U.S.C. § 119(e) and the benefit of U.S. Provisional Application No. 61/245,732 entitled EASY REMOVABLE COMBUSTION TUBE, filed on Sep. 25, 2009, by Gordon C. Ford, et al., the entire disclosures of which are incorporated herein by reference.

BACKGROUND OF THE INVENTION

The present invention relates to a combustion furnace for an analyzer and particularly to the removable mounting of a combustion tube therein.

The combustion of inorganic solid samples using an induction furnace requires a pressurized oxygen-rich environment. A quartz combustion tube is typically used to maintain this pressurized environment but becomes coated with byproducts of combustion during the combustion process. The quartz tube must be cleaned and eventually replaced to maintain the accuracy of sample results. The mounting of a combustion tube in existing furnaces equipped with an auto cleaner is both time consuming and cumbersome, requiring that fluid fittings and electrical connections be removed and the auto-cleaner device removed from the combustion tube area of the furnace. The combustion tube is removed from the front of the furnace housing once the disassembly has been completed. Once a new combustion tube has been installed, the furnace has to be reassembled, frequently including the connection of fluid couplings which can lead to leaks in the system if not properly accomplished. Thus, the maintenance, removal and replacement of combustion tubes in existing furnaces is difficult, time consuming, and leads to downtime for the operation of an analyzer.

Accordingly, there exists a need for an improved analytical combustion furnace in which a combustion tube can be readily accessed without disconnecting fluid fittings, auto-cleaners, or the like from the furnace assembly.

SUMMARY OF THE INVENTION

The system of the present invention accomplishes this goal by providing a combustion tube mounting system in which the combustion tube is removably installed through an aperture in the floor of the furnace housing. The combustion tube can be manually or automatically unlocked from the floor of the furnace housing by a cam-locking mechanism for positioning the combustion tube in an open area of the furnace below the furnace housing for easy removal and replacement.

In a preferred embodiment, a combustion tube includes a base seal assembly which is placed on the lower seal assembly and raised to automatically align with the upper furnace seal. Cams in the floor of the furnace housing engage a cam associated with the base seal assembly to lock the combustion tube in place as it is raised into the furnace housing. As a result of this downwardly removable combustion tube, the steps of disassembling the furnace components, including the self-cleaning mechanism located above the combustion tube, is eliminated as is the necessity for skilled technicians to replace the combustion tube. An operator can easily unlock the combustion tube from the furnace and lower it for access and replacement.

These and other features, objects and advantages of the present invention will become apparent upon reading the following description thereof together with reference to the accompanying drawings.

DETAILED DESCRIPTION OF THE PREFERRED EMBODIMENT

Figure 1:
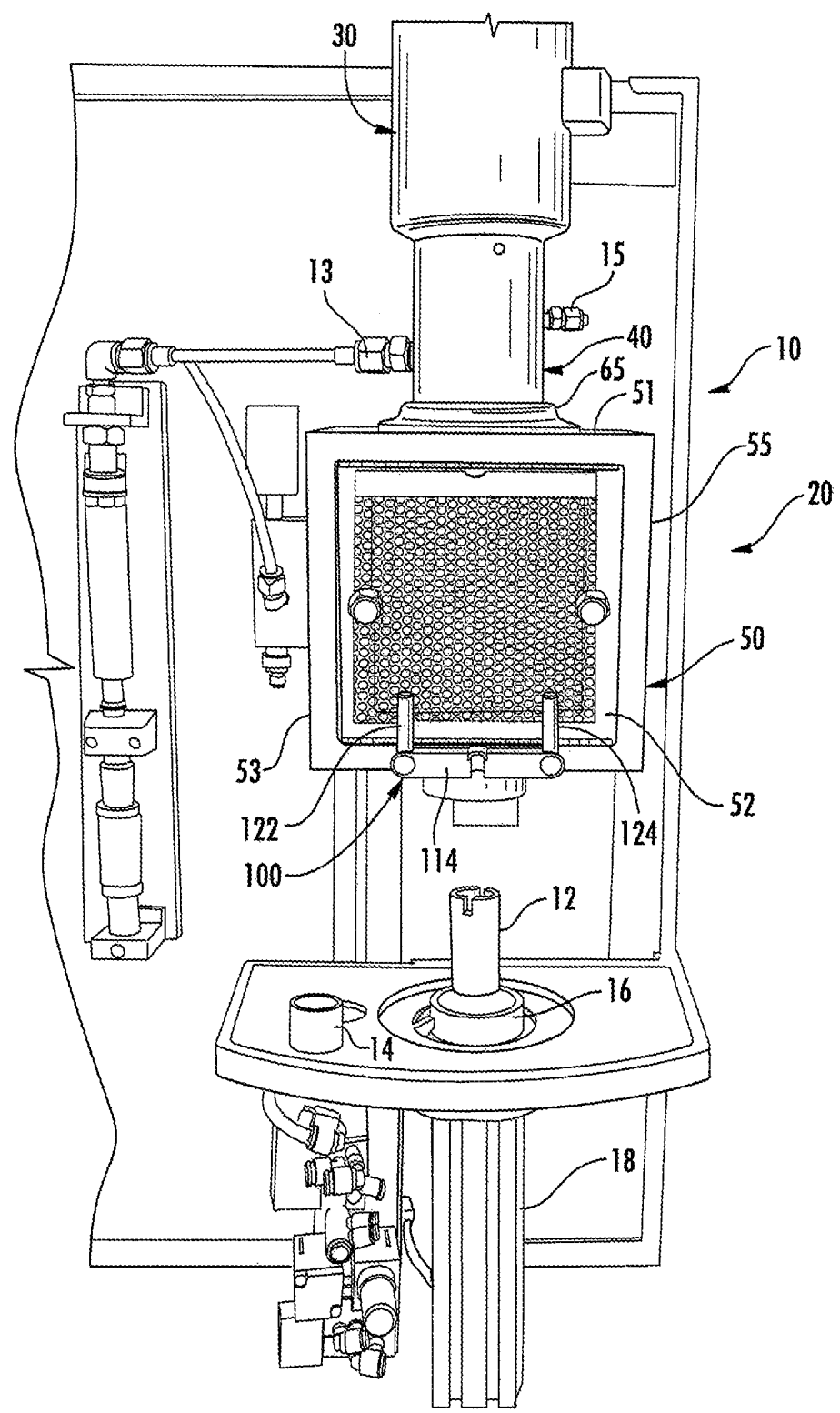
FIG. 1 is a front perspective view of a furnace embodying the present invention.

Referring initially to FIG. 1, there is shown an analyzer 10 which includes an induction furnace assembly 20, including the auto cleaning mechanism 30 described in detail in U.S. Provisional Patent Application Ser. No. 61/373,014, filed Aug. 12, 2010, entitled COMBUSTION FURNACE AUTO CLEANER, the disclosure of which is incorporated herein by reference. The analyzer components themselves can be similar to those employed in a carbon sulfur analyzer, Model No. CS600, available from Leco Corporation of St. Joseph, Mich. The analyzer 10 is shown in FIG. 1 with the cover shrouds removed to expose the components of the induction furnace, which are also shown in FIGS. 2-5. The detachable auto cleaner assembly 30 is removably mounted by a bayonet connection to a heated filter assembly 40, which is sealably secured at 65 to the top wall 51 of combustion housing 50. Housing 50 additionally includes side walls 53 and 55, an interface back wall 57, and floor 58, as best seen in FIGS.

Figure 2:
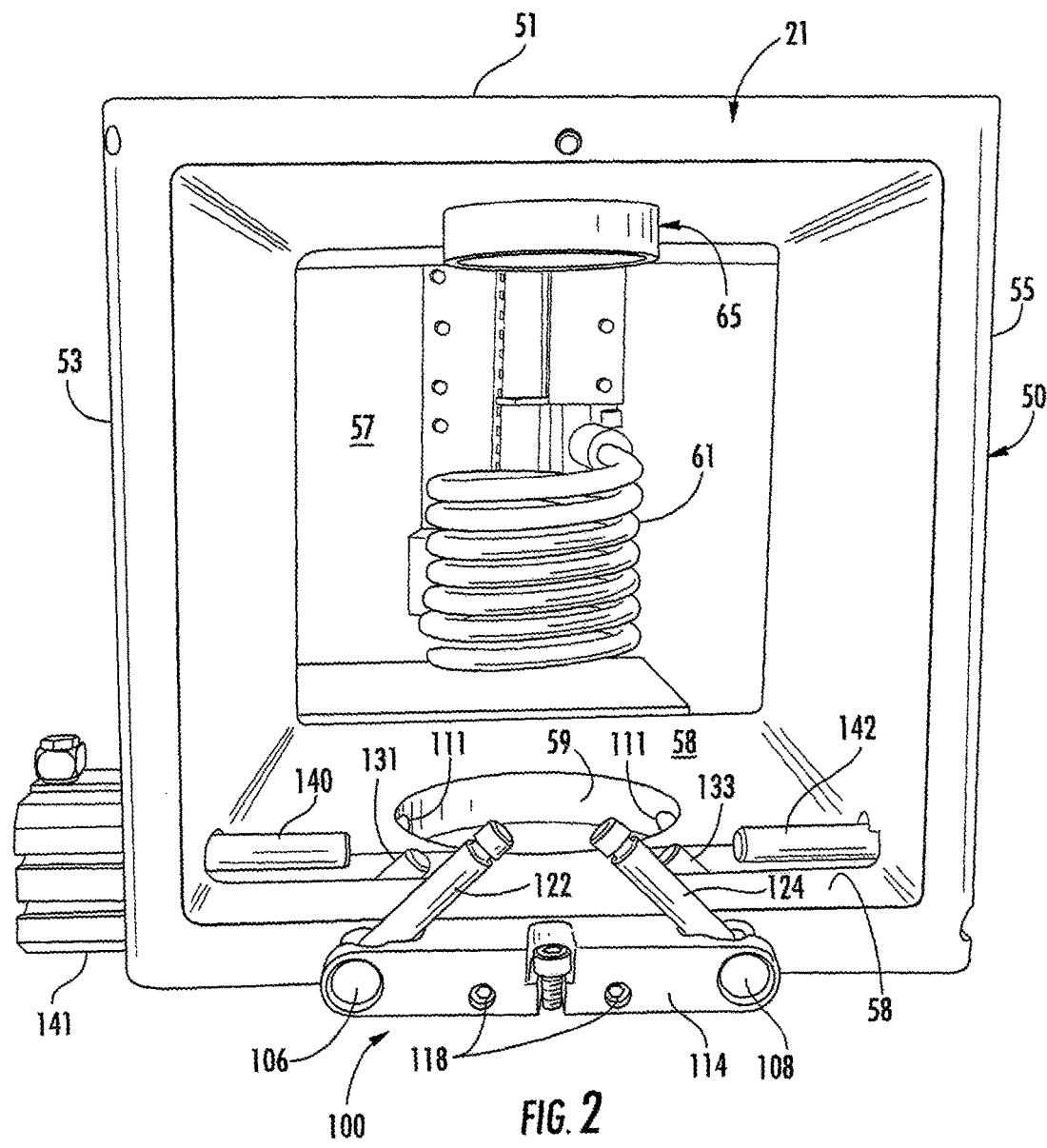
FIG. 2 is an enlarged front perspective view of the furnace housing with the cover removed showing the combustion tube locking mechanism in an unlocked position.

7-12. The housing 50 is mounted to structural base 17 of the analyzer 10, which includes housing 50. The front of furnace housing 50 is enclosed by a quickly removable door 52, which, when removed as seen in FIG. 2, exposes an induction coil 61 which surrounds a combustion tube 60 (FIG. 7) in a conventional manner to heat an analytical specimen held in a ceramic crucible 14 (FIG. 1) when introduced into the hot zone of combustion tube 60 by vertically movable pedestal 12. Tube 60 is sealably coupled to the lower end of filter assembly 40 by an upper seal assembly 65 in a conventional manner. The pedestal 12 (FIG. 1) for holding a sample-holding crucible 14 is positioned on a cup-shaped lower seal assembly 16 and is raised and lowered into combustion tube 60 by means of a pneumatic cylinder 18 and cylinder rod 22 (FIG. 7) coupled to assembly 16. In the position shown in FIG. 1, the cylinder rod 22 is in a lowered retracted position within cylinder 18.

A combustion tube base assembly 80 (FIGS. 3-5) sealably couples the lower end of tube 60 to lower seal assembly 16 such that, during combustion of a sample, oxygen flows upwardly through a gas inlet in assembly 16 to sweep byproducts of combustion into gas outlet 13 (FIG. 1) for analysis. Oxygen is also supplied to the upper end of combustion tube 60 by an oxygen inlet 15 and suitable passageways to an inlet lance to direct oxygen into crucible 14 during combustion. Housing 50 includes cam-actuated locking assembly 100 which cooperates with base assembly 80 to allow the combustion tube 60 to be easily withdrawn from underneath the floor of combustion housing 50, as described later.

Figure 3:
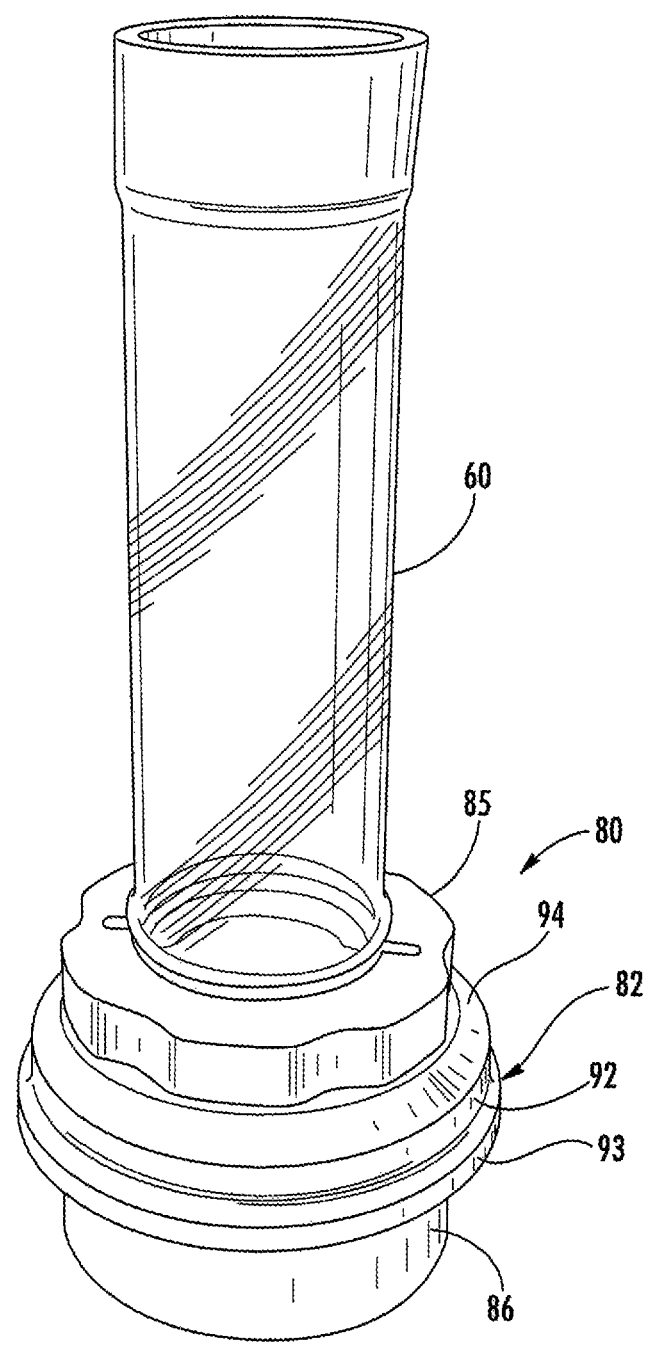
FIG. 3 is a perspective view of the combustion tube with its base seal assembly.
Figures 4, 5:
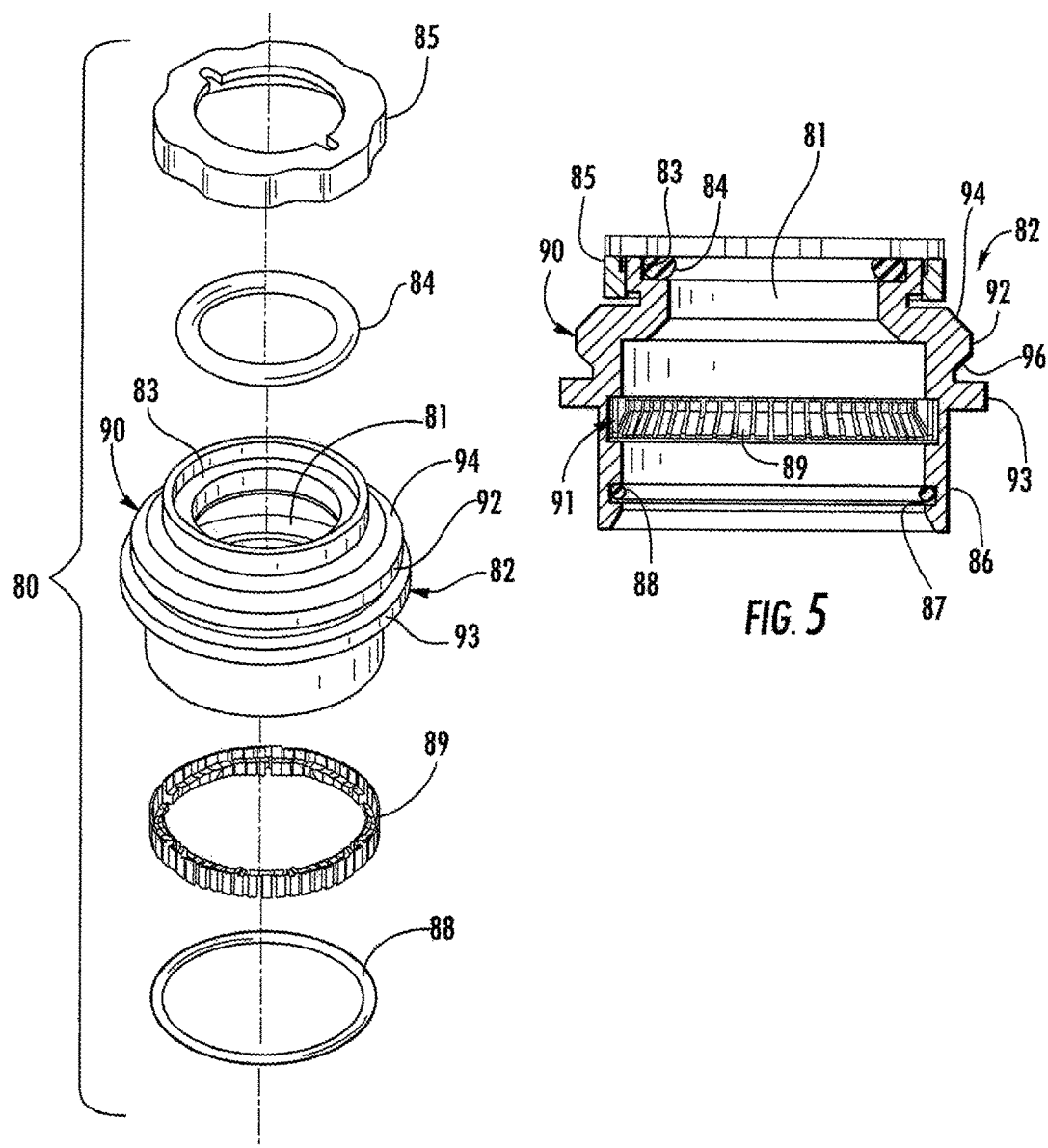
FIG. 4 is an exploded perspective view of the base seal assembly.
FIG. 5 is a cross-sectional view of the assembled base seal assembly.
Figure 6:
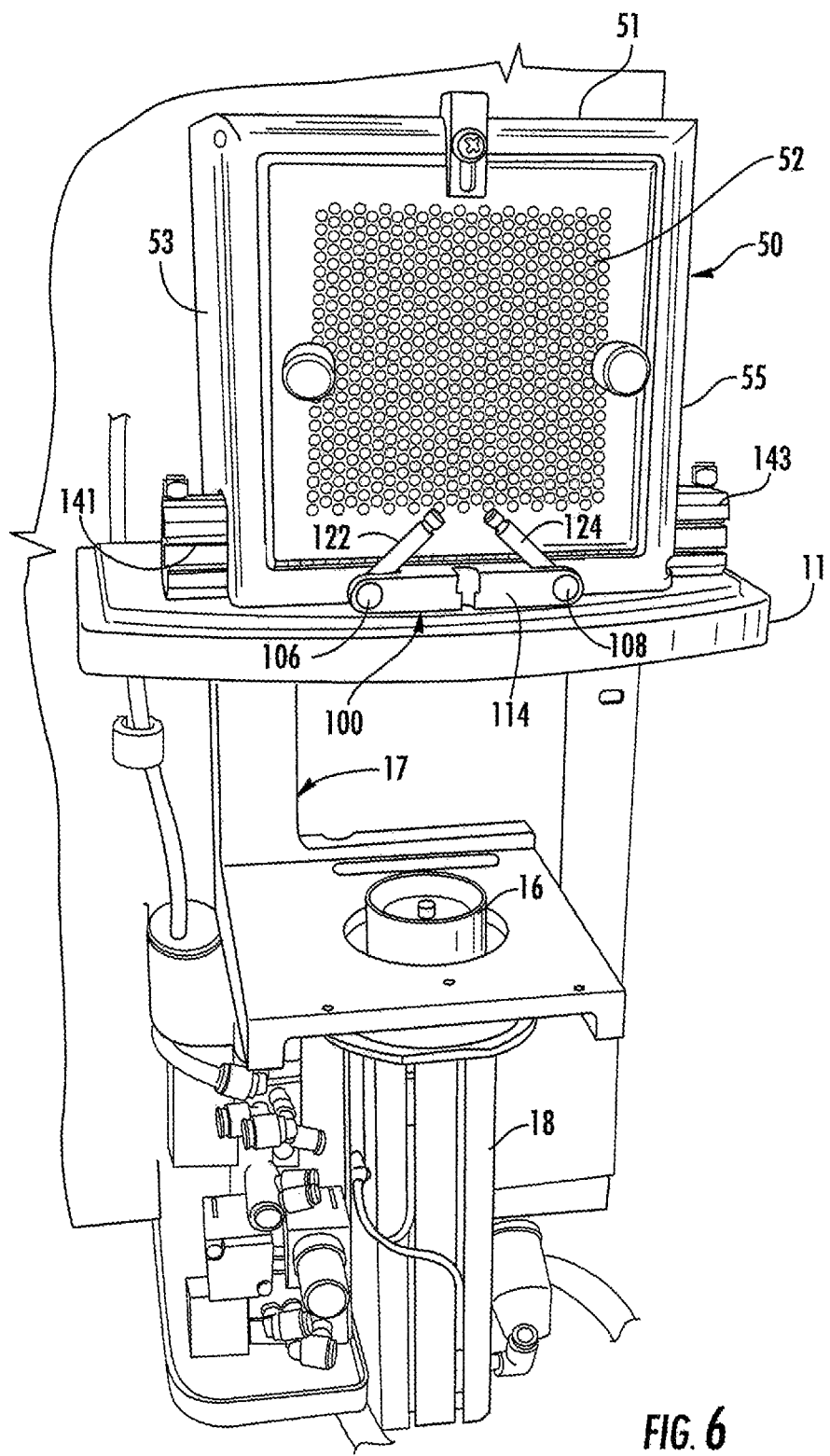
FIG. 6 is a front perspective view of the furnace shown with the locking mechanism in an unlocked position.

Combustion tube 60 can be a conventional quartz combustion tube available from Leco Corporation, Part No. 619-590-775 or its equivalent. The combustion tube, as seen in FIGS. 3-5, includes a base assembly 80 having a generally cylindrical collar 82 with a central aperture 81 therein for receiving the combustion tube 60, as seen in FIG. 3. Near the upper edge of collar 82 is an annular recess 83 for receiving an O-ring seal 84. A locking cap 85 is threaded onto collar 82 and compresses the O-ring seal once the combustion tube has been inserted therein for sealably holding the combustion tube within the collar 82. Collar 82 includes a lower cylindrical sleeve 86 having internal annular recess 87 for receiving a second O-ring 88 for sealing the base assembly 80 onto the lower seal assembly 16. Further, the assembly 80 includes a metal RFI shield 89 and a third sealing O-ring 78 (FIGS. 14 and 15) positioned within an annular recess 91 of collar 82.

Figure 14:
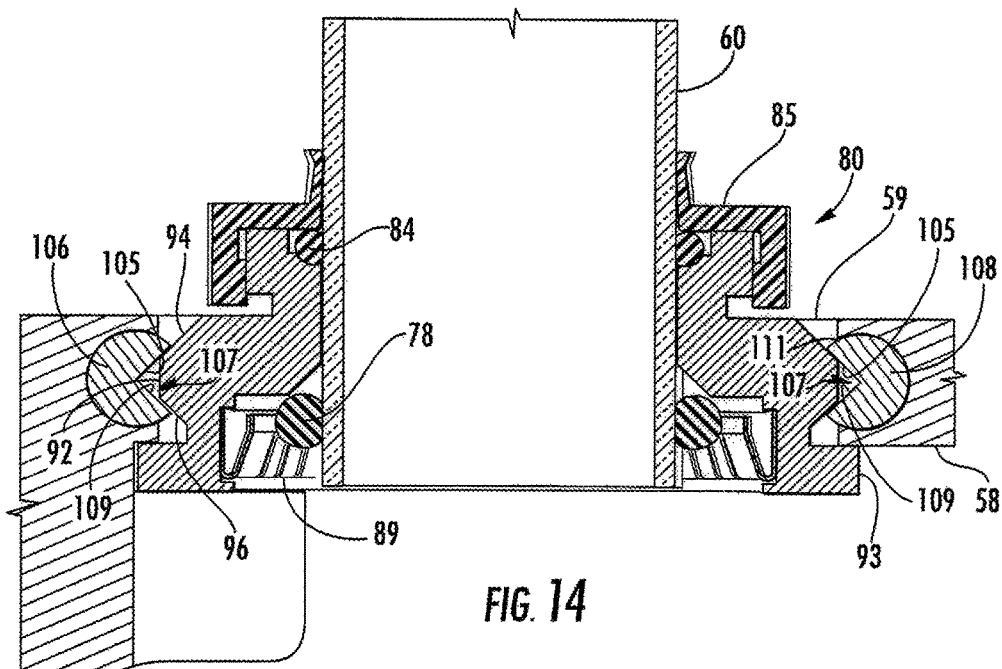
FIG. 14 is a fragmentary vertical cross-sectional view of a combustion tube shown in a locked position within the floor of the furnace housing.

Collar 82 includes a cam 90 which has an outer annular vertical surface 92, an upper chamfered surface 94 chamfered upwardly and inwardly at an angle of about 45° from the vertically extending annular surface 92 and a lowered chamfered surface 96 inwardly and downwardly beveled at an angle of about 45° from surface 92. The two surfaces thus form an angle of about 90° between them to fit (as described below with respect to FIG. 14) within a 90° slot 107. Collar 82 also includes an annular flange 93 having a diameter greater than aperture 59 in furnace housing floor 58 to engage the undersurface of floor 58 when the combustion tube is in an installed locked position as seen in FIG. 14. The cam 90 so-defined interengages with the cam pins 106 and 108 of cam-actuated assembly 100 for locking and unlocking the combined combustion tube 60 and base assembly 80 (shown in FIG. 3) as now described.

Figure 7:
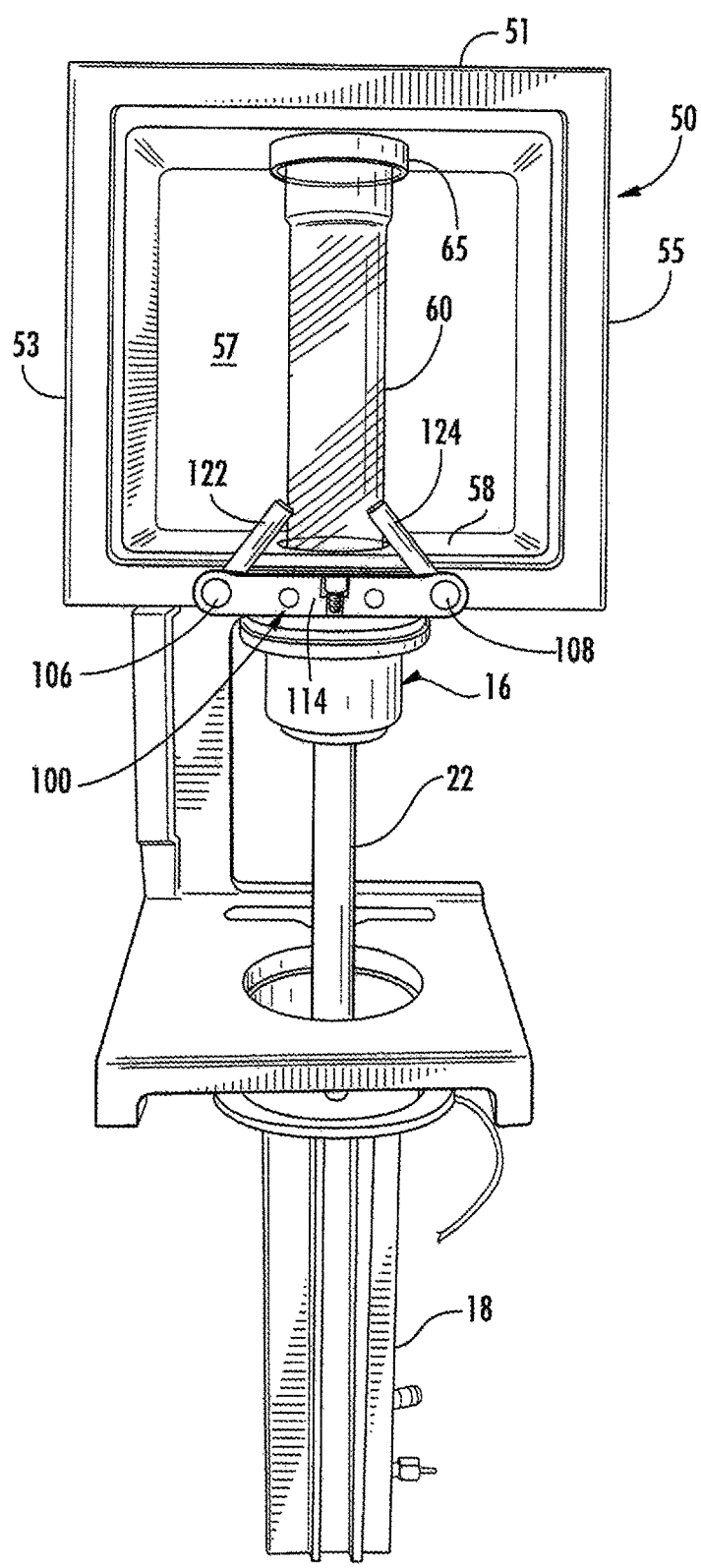
FIG. 7 is a partial front perspective view of the furnace shown in FIG. 6, shown with the cover removed.
Figure 8:
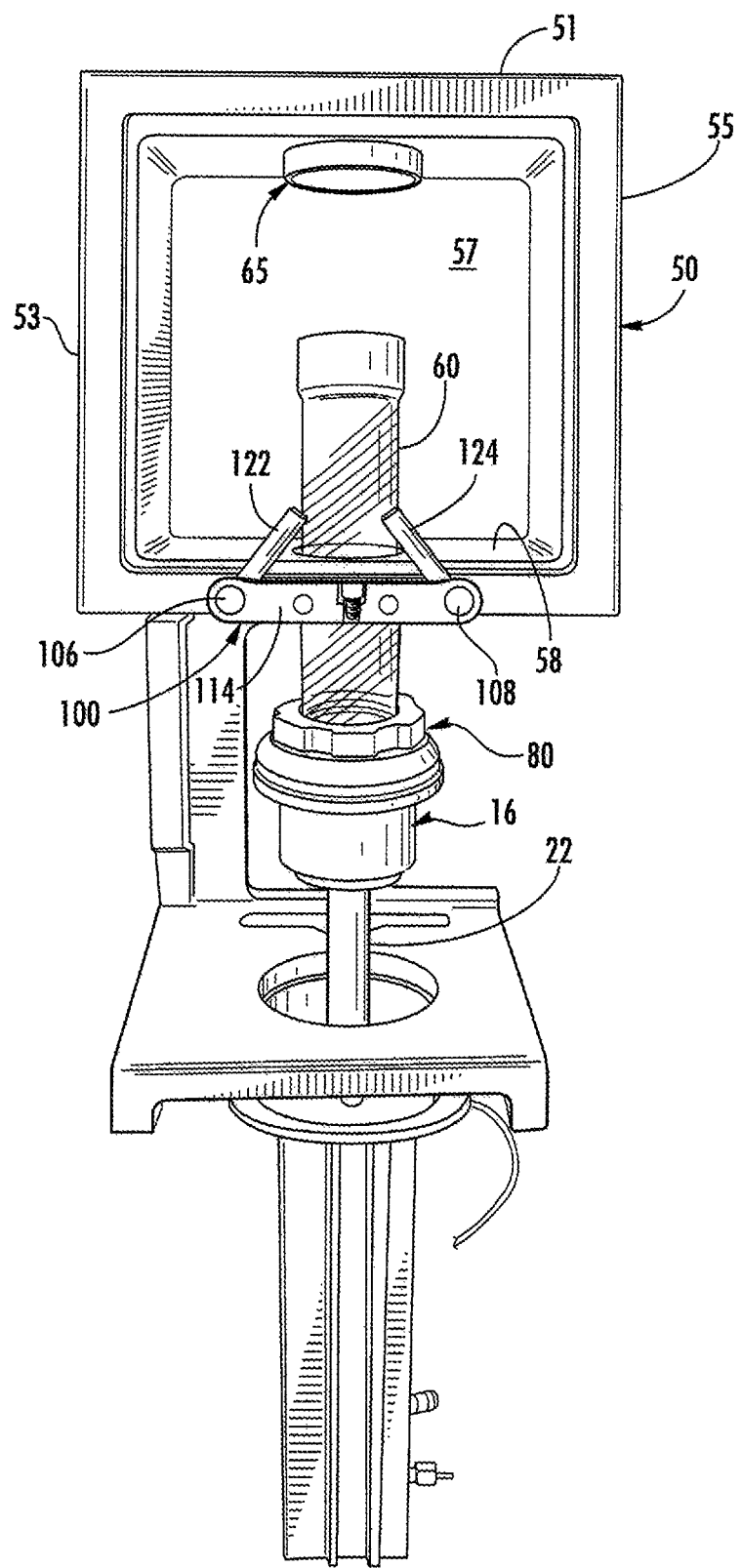
FIG. 8 is a front perspective view of the furnace shown in FIG. 7, showing the lowering and raising of the combustion tube through an aperture in the furnace housing floor.
Figure 9:
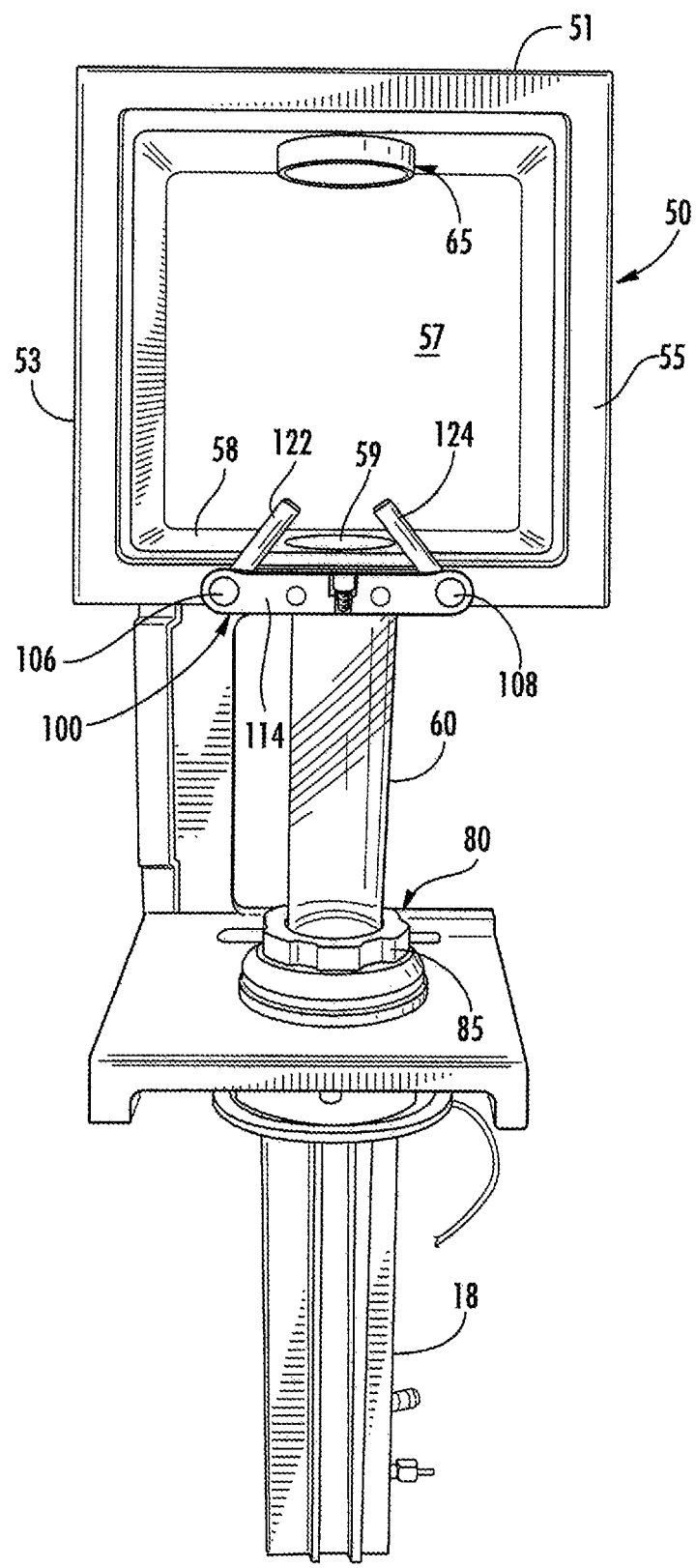
FIG. 9 is a front perspective view of the furnace shown in FIG. 8, showing the combustion tube lowered from the furnace housing in a position for removal/replacement.
Figure 10:
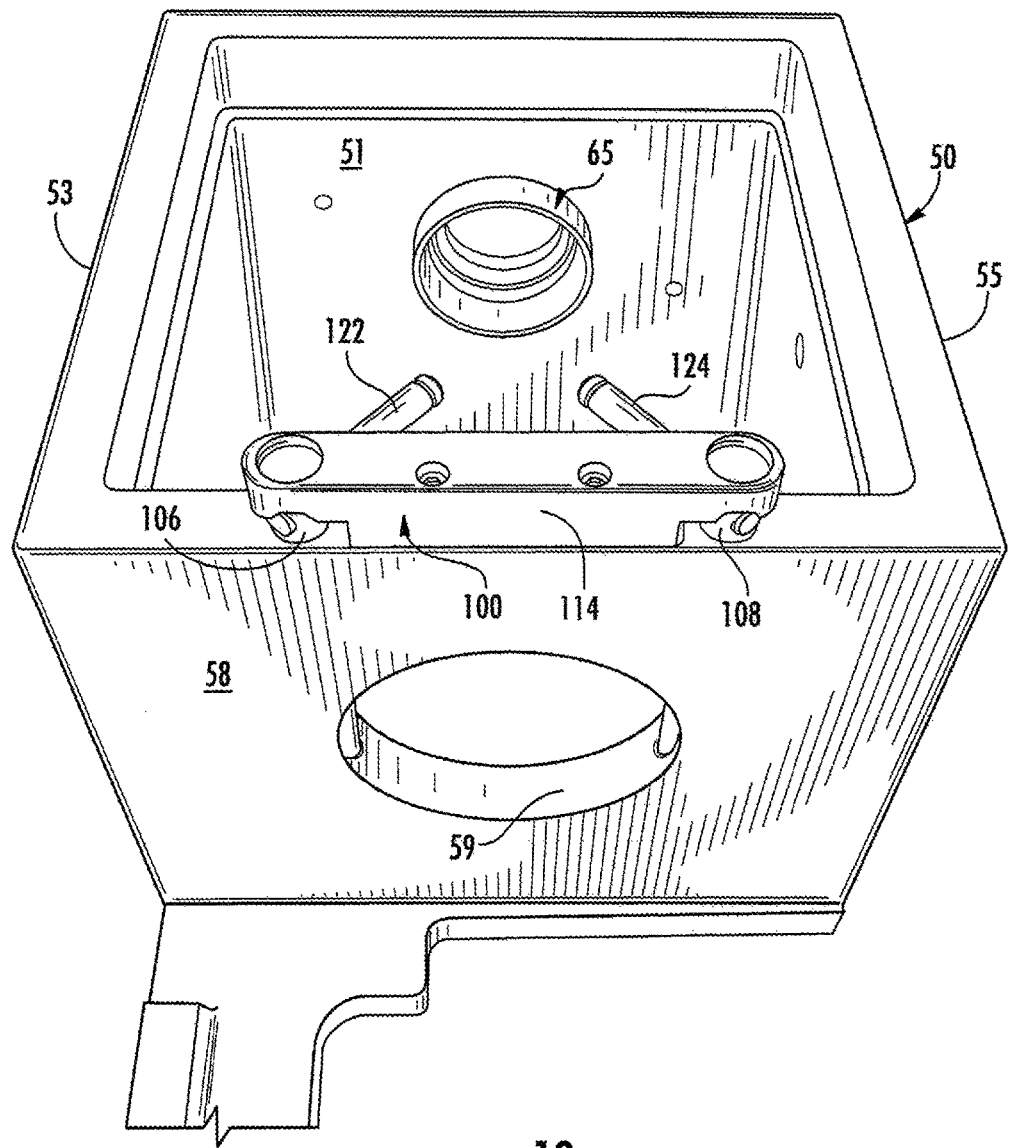
FIG. 10 is a bottom perspective view of the furnace housing.
Figure 11:
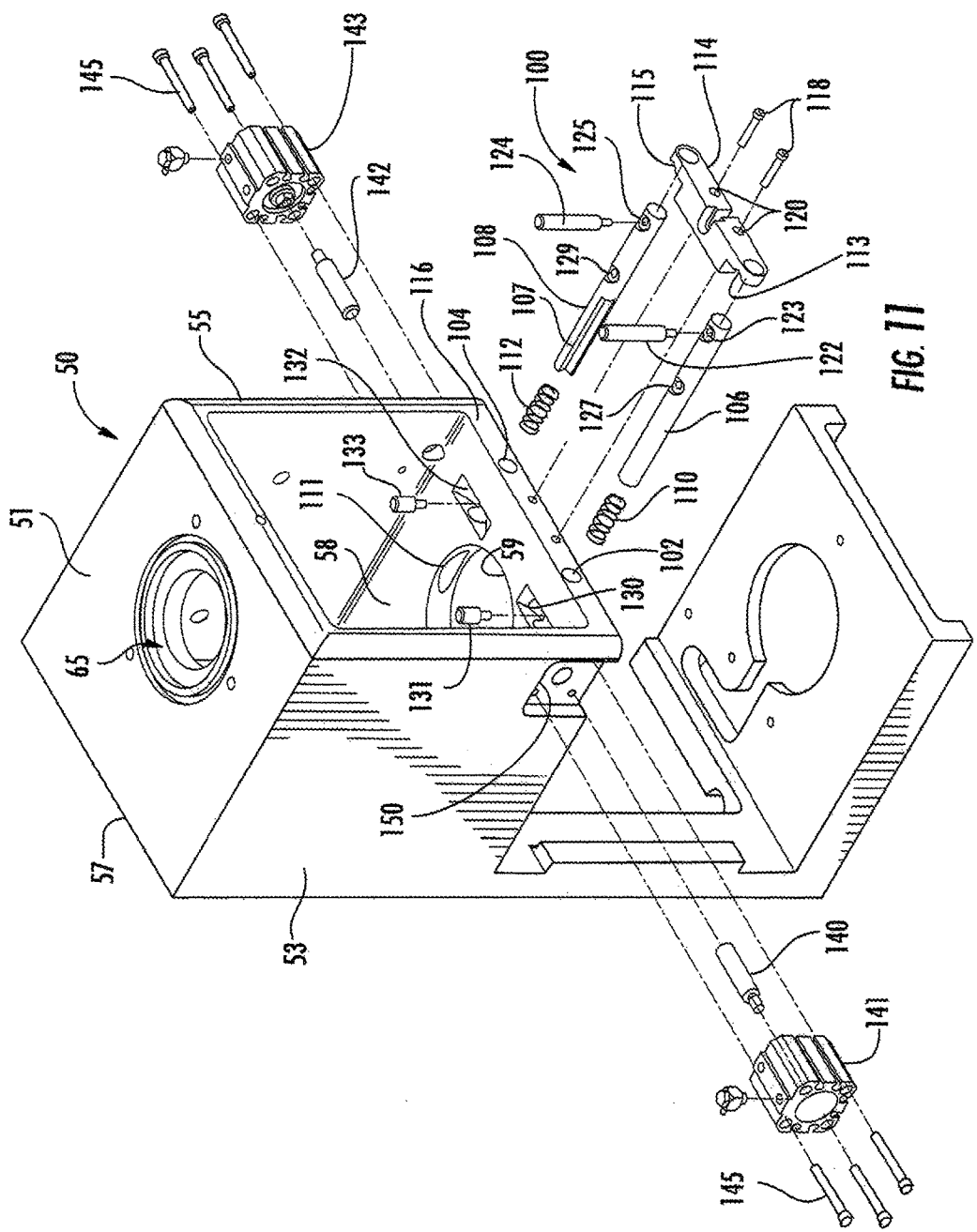
FIG. 11 is a left front exploded perspective view of the furnace housing and locking mechanism for the combustion tube.

FIGS. 7-15 illustrate the removal of the combustion tube 60 from the furnace housing 50 and, for purposes of clarity, the induction coils and other parts unnecessary to the description of the cam-actuated combustion tube mounting arrangement have been deleted from these figures. Also, in FIGS. 7-10, the pneumatic actuators for automatically operating the cam-actuated assembly 100 are not shown as these figures are primarily for the purpose of illustrating the motion of the combustion tube during its removal and replacement. FIGS. 7-9 illustrate the motion of the combustion tube when cylinder 18 is moved to a retracted position once the cam-actuated assembly 100 has been moved to an unlocked position allowing, as seen in FIG. 8, the combustion tube to be lowered through the circular aperture 59 (FIG. 10) in the floor 58 of furnace housing 50. When lowered to a position as seen in FIG. 9, the combustion tube 60 and base assembly 80 can be lifted from the lower seal assembly 16 and combustion tube 60 replaced with a new combustion tube by loosening locking ring 85, allowing the tube to be removed from the base assembly 80. The cam-actuated assembly 100 cooperates with the cam 90 of the combustion tube base assembly 80 to form a releasable locking mechanism to lockably hold and alternately release the combustion tube 60 from below the furnace housing 50.

Figure 15:
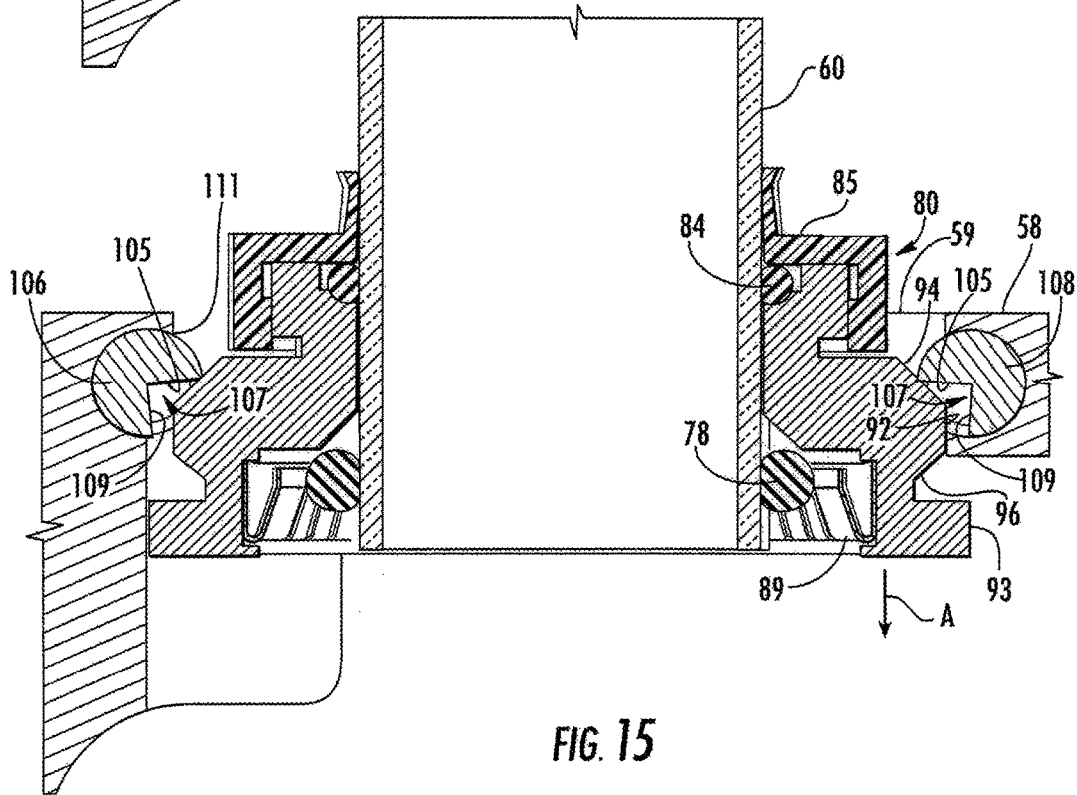
FIG. 15 is a fragmentary vertical cross-sectional view showing the combustion tube in an unlocked position for removal.

Assembly 100 is used for either manually or automatically unlocking the combustion tube 60 (and attached base assembly 80) from the combustion housing 50 as best seen in FIGS. 11-15. Floor 58 of combustion housing 50 includes a pair of blind cylindrical apertures 102 and 104, which rotatably receive cam pins 106 and 108 of mechanism 100. Apertures 102 and 104 are formed and sized to intersect opposite edges of aperture 59 in floor 58 and are positioned such that generally V-shaped 90° slots 107 on the inner-facing edges of pins 106 and 108 are exposed through openings 111 in the so truncated cylindrical side wall of aperture 59. Springs 110 and 112 engage the inner ends of pins 106 and 108, which are retained within the apertures 102 and 104 by a mounting plate 114 secured to the front face 116 of floor 58 by fasteners 118 extending through apertures 120 in mounting plate 114. A pair of manually actuated handles 122 and 124 are pinned to apertures 123 and 125, respectively, near the ends of cam pins 106, 108, such that pins 106 and 108 can be manually rotated by the manipulation of the operator of handles 122 and 124 rotating them inwardly, as seen, for example, in FIGS. 7-10, to an unlocking position. Springs 110, 112 urge handles 122, 124 into concave recesses 113, 115 on the inner facing surface of plate 114 urging them into a releasable locked position (FIGS. 1 and 12-14). In the unlocked position illustrated in FIG. 15, the handles are rotated out of recesses 113, 115 rotating the 90° slots 107 of pins 106 and 108 to a position in which surfaces 105 and 109 of slots 107, which normally engage the chamfers 94 and 96 on cam 90 of assembly 80, respectively, release cam 90 allowing, as seen in FIG. 15, the combustion tube 60 and base assembly 80 to be lowered downwardly in the direction indicated by arrow A for removal when in the position shown in FIG. 9. Surfaces 105 and their tip junction with cylindrical pins 106 and 108 also urge against chamfer 94 of cam 90 to assist in freeing base assembly 80 and combustion tube 60 downwardly from floor 50.

Figure 12:
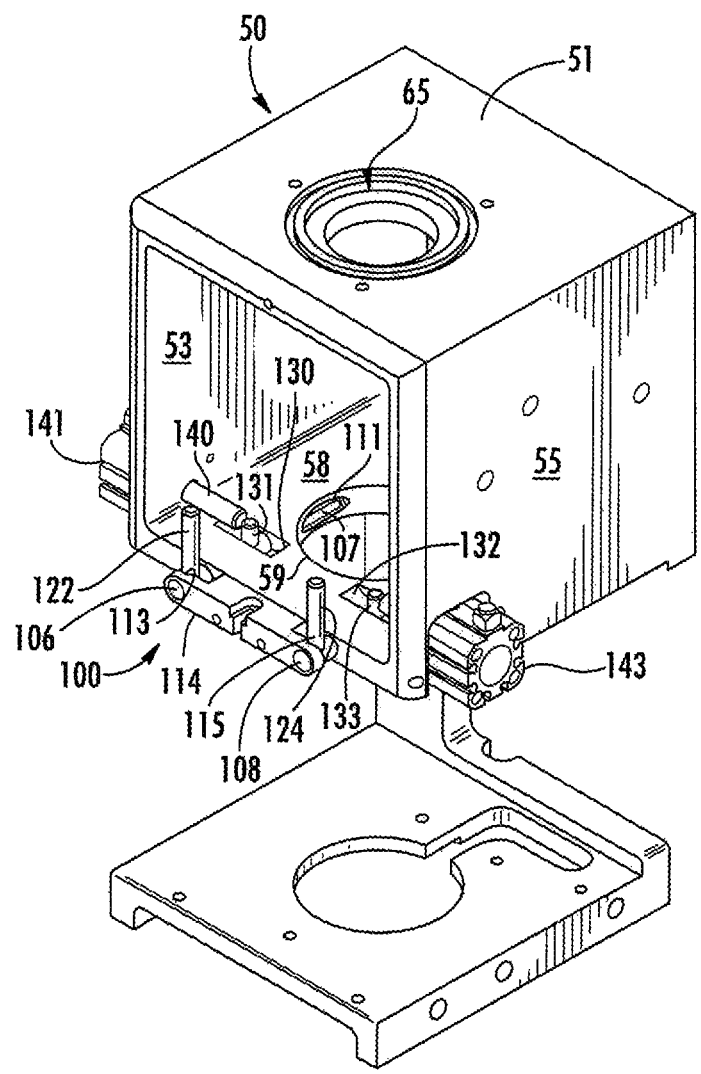
FIG. 12 is a right front perspective view of the assembled furnace housing.
Figure 13:
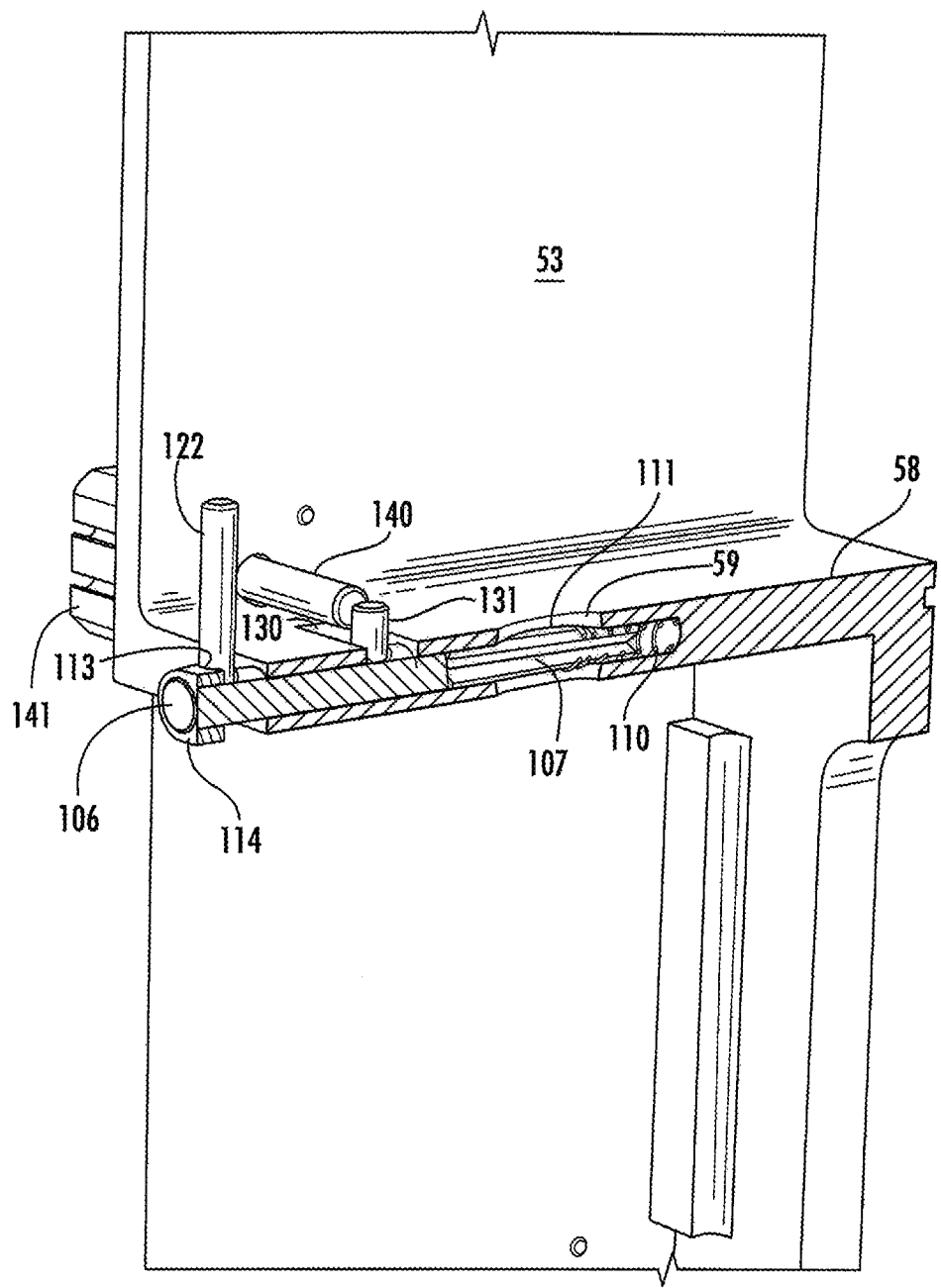
FIG. 13 is a fragmentary vertical cross-sectional view of the cam locking mechanism for the combustion tube.

The cam-actuated combustion tube releasing assembly 100 can either be manually actuated by an operator squeezing the handles 122, 124 toward one another to rotate pins 106, 108 and release the combustion tube 60 or the operation can be automated. For such purpose, floor 58 includes a pair of arcuate recesses 130 and 132 forwardly of aperture 59 in floor 58 and which communicate with apertures 102 and 104 to expose apertures 127 and 129 (FIG. 11) on pins 106 and 108, which receive actuator pins 131 and 133. Pins 131, 133 extend upwardly from floor 58 and can be engaged, as best seen in FIGS. 12 and 13, by actuator rods 140 and 142 of pneumatic cylinders 141 and 143, respectively. Cylinders 141 and 143 are secured within recesses 150 in the side walls 53 and 55 of the housing 50 by fasteners 145 in a conventional manner. Thus, the cam-actuated assembly 100 can either be manually entered by the operator engaging handles 122 or 124 or electrically by the actuation of cylinders 141 and 143 to rotate the pins 106 and 108 from a locking position, shown in FIG. 14, to an unlocked position, shown in FIG. 15. When in the unlocked position, the combustion tube and its seal assembly can be dropped downwardly utilizing cylinder 18 to lower the combustion tube 60 into the position shown in FIG. 9 where it can be removed from the furnace housing and replaced.

Once the combustion tube has been replaced with a new tube and mounted to the base assembly 80, the cylinder 18 can then be actuated, reversing the process by raising the combustion tube in an upwardly direction, as seen in FIG. 8, to a locked position shown in FIG. 1. As the combustion tube is raised through aperture 59, the surface 94 of cam 90 engages the camming surface 105 on pins 106 and 108 rotating them when combustion tube 60 is moved in the direction opposite arrow A in FIG. 15, to again move the locking pins 106, 108 to the locked position illustrated in FIG. 14. In this position, surfaces 105, 109 on pins 106, 108 engage the chamfered surfaces 94, 96, respectively, of cam 90 and securely hold the combustion tube 60 in place with the flange 93 of the base assembly engaging the lower surface of floor 58 of the furnace housing 50. As seen in FIG. 15, the pins 106 and 108 extend sufficiently outwardly through slots 111 in the cylindrical side wall of aperture 59 so as to engage cam 90.

It will become apparent to those skilled in the art that various modifications to the preferred embodiment of the invention as described herein can be made without departing from the spirit or scope of the invention as defined by the appended claims.

The invention claimed is:

1. A combustion furnace and combustion tube assembly for an analyzer comprising:
    a generally cylindrical combustion tube;
    a furnace housing having a floor positioned at a lower end of said housing, said floor having an aperture therein allowing said combustion tube to be removed through said floor;
    a releasable locking mechanism extending between said combustion tube and said floor for alternately holding said combustion tube in a use position and releasing said combustion tube for removal downwardly through said aperture; and
    wherein said releasable locking mechanism includes a base assembly secured near one end of said combustion tube for releasably holding said combustion tube, wherein said base assembly comprises a collar including a cam, a locking cap surrounding said combustion tube and threadably coupled to said collar and a first annular seal positioned between said locking cap and said collar.

2. The assembly as defined in claim 1 wherein said cam of said collar has an annular outer surface and upper and lower chamfered surfaces spanning opposite sides of said annular surface.

3. The assembly as defined in claim 2 wherein said collar has an internal annular recess opposite said locking cap and includes a second annular seal positioned in said recess.

4. The assembly as defined in claim 3 wherein said collar further includes a cylindrical sleeve extending in spaced relationship to said lower chamfered surface, wherein said sleeve includes an annular recess receiving a third annular seal, said sleeve shaped to sealably extend over a furnace lower seal assembly.

5. The assembly as defined in claim 4 and further including a lower seal assembly selectively coupled to said base assembly and movable between a raised position and a lowered position for raising said combustion tube into said furnace housing and lowering said combustion tube from said furnace housing through said aperture in said floor.

6. A combustion furnace and combustion tube assembly for an analyzer comprising:
    a combustion tube;
    a furnace housing having a floor with an aperture therein for allowing said combustion tube to pass through said floor; and
    a releasable locking mechanism extending between said combustion tube and said floor for alternately holding said combustion tube in a use position and releasing said combustion tube for removal downwardly through said aperture wherein said releasable locking mechanism comprises a cam secured near one end of said combustion tube for releasably holding said tube in said combustion furnace housing, and at least one cam pin rotatably mounted to said combustion furnace housing adjacent said aperture for releasably engaging said cam.

7. The assembly as defined in claim 6 wherein said locking mechanism includes at least a pair of cam pins on opposite sides of said aperture in said floor.

8. The assembly as defined in claim 7 wherein said cam includes a pair of spaced-apart beveled surfaces extending at about 90° with respect to each other.

9. The assembly as defined in claim 8 wherein said cam pins include tapered slots with side walls angled at about 90°, which side walls engage said beveled surfaces of said cam to hold said combustion tube in place.

10. The assembly as defined in claim 9 wherein said cam pins include handles for rotating said cam pins between a cam engaging position and a cam disengaging position.

11. The assembly as defined in claim 10 wherein said locking mechanism further includes actuators for rotating said cam pins.

12. A combustion tube assembly for a combustion furnace comprising:
    a combustion furnace housing having a floor with an aperture therein for receiving a combustion tube;
    a general cylindrical combustion tube;
    a collar extending around said combustion tube;
    at least one O-ring seal sealably coupling said combustion tube to said collar, wherein said assembly includes a pair of O-ring seals located near opposite ends of said collar; and
    wherein said assembly further includes a locking mechanism cooperating with said floor of said combustion furnace and said collar for alternately holding said combustion tube in a use position and releasing said combustion tube for removal downwardly through said aperture in said floor, wherein said collar includes a cam secured near one end of said combustion tube for releasably holding said tube in said combustion furnace housing, and at least one cam pin rotatably mounted to said combustion furnace housing adjacent said aperture for releasably engaging said cam of said collar.

13. The assembly as defined in claim 12 wherein said locking mechanism includes at least a pair of cam pins on opposite sides of said aperture.

14. The assembly as defined in claim 13 wherein said cam includes a pair of spaced-apart beveled surfaces extending at about 90° with respect to each other.

15. The assembly as defined in claim 14 wherein said cam pins include tapered slots with side walls angled at about 90°, which side walls engage said beveled surfaces of said cam to hold said combustion tube in place.

16. The assembly as defined in claim 15 wherein said cam pins include handles for rotating said cam pins between a cam engaging position and a cam disengaging position.

17. The assembly as defined in claim 16 wherein said locking mechanism further includes actuators for rotating said cam pins.

* * * * *